US006109360A

United States Patent [19]

Mandzukic et al.

[11] Patent Number: 6,109,360

[45] Date of Patent: Aug. 29, 2000

[54] FIRE FIGHTING MONITOR

[75] Inventors: Thomas Mandzukic, North Royalton; Mark S. Saner, Wooster, both of Ohio

[73] Assignee: Premier Farnell Corp., Cleveland, Ohio

[21] Appl. No.: 09/243,693

[22] Filed: Feb. 3, 1999

Related U.S. Application Data

[60] Provisional application No. 60/073,700, Feb. 4, 1998.

[51] Int. Cl.[7] .......... A61L 9/04

[52] U.S. Cl. .......... 169/51; 239/587.1

[58] Field of Search .......... 239/587.1, 587.2, 239/587.5; 169/51, 52, 24

[56] References Cited

U.S. PATENT DOCUMENTS

| | | | |
|---|---|---|---|
| 1,583,772 | 5/1926 | Blaw . | |
| 1,880,272 | 10/1932 | Panther, Jr. | 239/587.2 |
| 1,961,481 | 6/1934 | Downs . | |
| 2,011,446 | 8/1935 | Judell . | |
| 2,986,344 | 5/1961 | Knight | 239/587.2 |
| 3,106,247 | 10/1963 | Lacks et al. . | |
| 3,666,179 | 5/1972 | Peschcke-Koedt | 239/587.2 |
| 3,770,062 | 11/1973 | Riggs . | |
| 3,893,630 | 7/1975 | Bochmann et al. . | |
| 4,007,793 | 2/1977 | Hux et al. . | |
| 4,674,686 | 6/1987 | Trapp . | |
| 4,793,557 | 12/1988 | Marchese et al. . | |
| 4,975,993 | 12/1990 | Black et al. . | |
| 4,984,745 | 1/1991 | Akeel et al. . | |
| 5,301,756 | 4/1994 | Relyea et al. . | |
| 5,362,279 | 11/1994 | Galchefski | 474/112 |
| 5,626,194 | 5/1997 | White . | |
| 5,788,158 | 8/1998 | Relyea | 169/24 |

*Primary Examiner*—Andres Kashnikow
*Assistant Examiner*—Christopher S. Kim
*Attorney, Agent, or Firm*—Jones, Day, Reavis & Pogue

[57] ABSTRACT

A fire fighting monitor having a rotatable extension member for adjusting the elevation of an outlet attached to the extension member while maintaining the discharge direction of the outlet relative to the horizontal.

14 Claims, 2 Drawing Sheets

FIRE FIGHTING MONITOR

RELATED APPLICATIONS

This application claims subject matter disclosed in U.S. provisional application Ser. No. 60/073,700 filed Feb. 4, 1998, the benefit of the filing date of which is hereby claimed.

BACKGROUND OF THE INVENTION

This application relates to the art of fire fighting monitors and, more particularly, to fire fighting monitors that are adapted to be mounted on the deck of a fire fighting apparatus such as a fire truck. Although the invention is particularly applicable to fire fighting monitors and will be described with specific reference thereto, it will be appreciated that the invention has broader aspects and can be used in other liquid discharge devices.

Typical fire fighting monitors that are mounted on the deck of a fire fighting apparatus are fixed in height, and the only adjustment is in the discharge angle of the water stream relative to the horizontal. If the fixed height is high enough to clear surrounding fixtures on the fire fighting apparatus such as lights and hose beds, the monitor may be to high to clear obstacles such as garage doors or bridges above underpasses. If the fixed height is sufficiently low to readily clear such obstacles, the water stream may strike fixtures mounted on the apparatus and deflect the water stream or damage the fixtures.

Accessories are available for increasing the elevation of the water outlet on a fixed height monitor. One arrangement uses an extension pipe that is positioned below the monitor and raises the water outlet by approximately 18 inches. Use of the extension pipe requires removal and reassembly of the monitor, and a separate storage space is required for the extension pipe when it is not being used. Another arrangement uses a telescopic extension pipe positioned below the monitor. Significant lifting force is required to lift the telescoping pipe along with the monitor to increase the elevation of the water outlet. In addition, extensive modifications are required below the deck of the fire fighting apparatus to accommodate the telescopic extension pipe. Such modifications occupy valuable space along with adding weight and complexity to the apparatus as well as cost.

It would be desirable to have a simplified arrangement for varying the elevation of the water outlet on a fire fighting monitor.

SUMMARY OF THE INVENTION

A fire fighting monitor adapted to be mounted on the deck of a fire fighting apparatus includes a water inlet member that is rotatable about a vertical axis. An extension member has one end connected with the inlet member for rotation about a first horizontal axis and the opposite end of the extension member has an outlet member attached thereto for rotation about a second horizontal axis.

With an arrangement of the type described, lifting of the extension member by rotating it about the first horizontal axis increases the elevation of the outlet member by an amount that is approximately the same as the length of the extension member between the two horizontal axes of rotation.

The monitor may be transported with the extension in a lowered storage position and rotated to a vertical position for fire fighting.

The outlet member has a discharge outlet, and a mechanism is provided for maintaining the discharge angle of the outlet during raising and lowering movement of the extension member.

The angle of the discharge outlet relative to the horizontal is selectively adjustable by rotating it relative to the extension member. Once the angle of the outlet member is adjusted, its desired orientation is maintained during rotational raising and lowering movement of the extension member. This is accomplished by providing a motion translation mechanism that imparts a degree of rotation to the outlet member that is equal and opposite to the degree of rotation imparted to the extension member.

In a preferred arrangement, the extension member is rotatably adjustable between a vertical position in which it extends vertically upward from the first horizontal axis and a lowered position in which it is inclined downwardly below the horizontal from the first horizontal axis.

The outlet member is adjustable between a vertical position in which the outlet discharges vertically upward and a downward discharge position in which the outlet projects a water stream below the horizontal.

In a preferred arrangement, both the extension member and the outlet member are independently rotatable through an arc of at least 135° in one direction from the vertical.

It is a principal object of the invention to provide a fire fighting monitor that allows adjustment in the elevation of the water discharge outlet.

It is a further object of the invention to provide such a fire fighting monitor that permits adjustment of in the elevation of the water discharge outlet in a manner that is relatively simple and takes very little time.

It is another object of the invention to provide such a fire fighting monitor in which the discharge angle of the water stream is automatically maintained during adjustments in elevation.

It is an additional object of the invention to provide such a fire fighting monitor that occupies a relatively small space and is reliable in operation.

DESCRIPTION OF A PREFERRED EMBODIMENT

Figure 1:
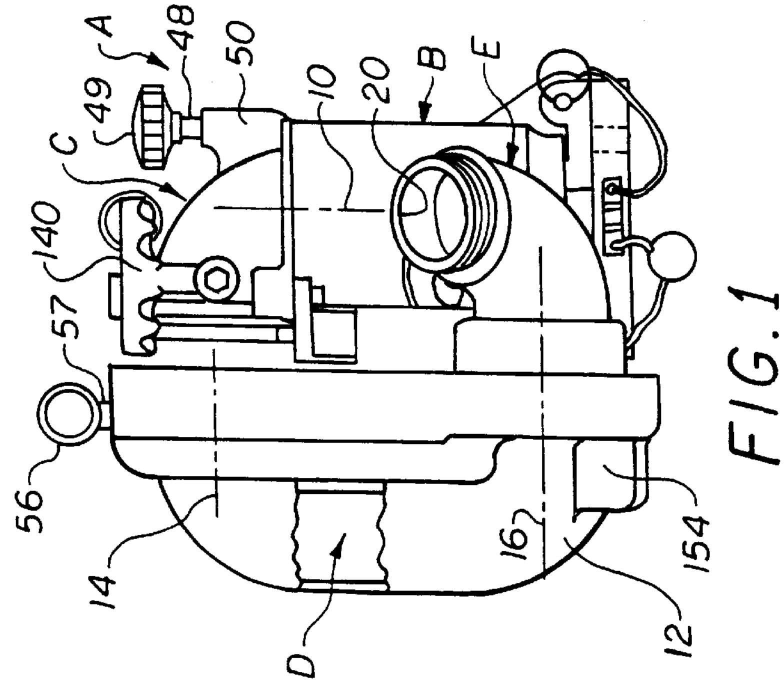
FIG. 1 is a front elevational view of a fire fighting monitor constructed in accordance with the present application.

Referring now to the drawing, wherein the showings are for purposes of illustrating a preferred embodiment of the invention only and not for purposes of limiting same, FIG. 1 shows a fire fighting apparatus A constructed in accordance with the present application. An inlet connector B has an inlet member C connected thereto for rotation about a vertical axis 10. An extension member D beneath cover shield 12 has one end connected with inlet member C for rotation about a first horizontal axis 14, and its opposite end is connected with an outlet member E that rotates about a second horizontal axis 16.

Figure 2:
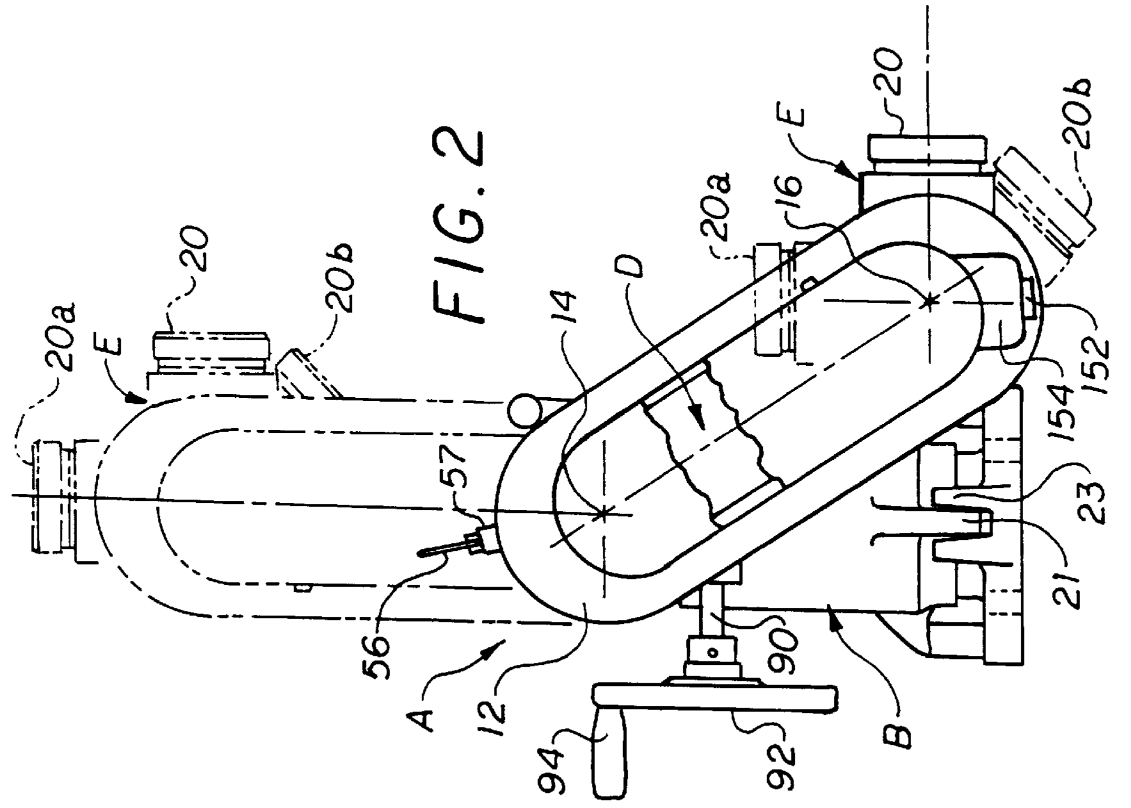
FIG. 2 is a side elevational view thereof and with an elevated position of an extension member shown in shadow lines.

Outlet member E has a water discharge outlet 20 and is shown in solid lines in a horizontal position in FIG. 2. Outlet member E is selectively adjustable between a vertical position shown in shadow lines at 20*a* and a downwardly inclined position indicated in shadow lines at 20*b*. In the vertical position shown at 20*a*, the outlet discharges water vertically upward. In the downwardly inclined position indicated at 20*b*, the outlet discharges water at an angle approximately 45° below the horizontal. The total angle between positions 20*a* and 20*b* is about 135°.

Extension member D is rotatable about first horizontal axis 14 to the vertical shadow line position shown in FIG. 2 in which it extends vertically upward from first horizontal axis 14. The degree of movement of extension member D between the solid line and shadow line positions of FIG. 2 is about 135°.

Figure 3:
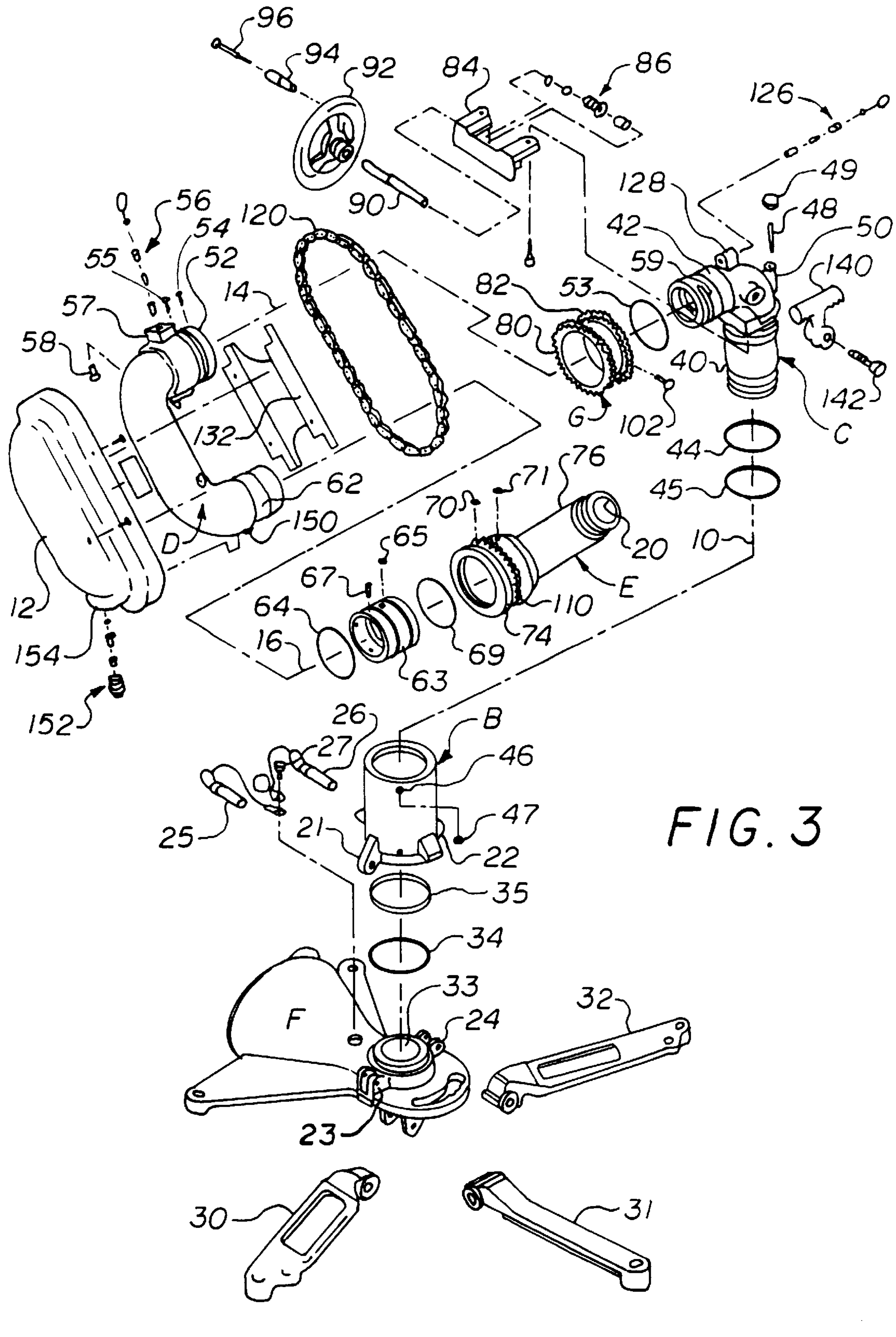
FIG. 3 is an exploded perspective illustration of a fire fighting monitor constructed in accordance with the present application.

With reference to FIG. 3, a water inlet ground support base member F includes ground supports 30, 31 and 32. Base member F has an outlet 33 and is attached to water inlet connector B with gasket 34 and retaining ring 35 interposed therebetween. Ears 21, 22 on inlet connector B arc received between double ears 23, 24 on base member F. All of the ears have aligned holes for receiving pins 25, 26 that are attached to wires that are tethered to base F by bolt 27. Removal of pins 25, 26 allows the entire monitor A to be lifted from ground support base F for attachment to a similar support flange that is bolted or otherwise secured to the deck of a fire fighting apparatus.

Inlet member C is a generally L-shaped elbow having a vertical portion 40 and a horizontal portion 42. Vertical portion 40 is received within inlet connector B for rotation relative thereto about a vertical axis, and sealing rings 44, 45 are provided between the exterior of vertical portion 40 and the interior peripheral surface of inlet connector B. The interior peripheral surface of inlet connector B and the external peripheral surface of vertical portion 40 of inlet elbow C have cooperating bearing races therein. A lateral hole 46 in the peripheral wall of inlet connector B permits installation of ball bearings between the races followed by closing of the hole with a plug 47.

A brake shaft 48 having a knob 49 on one end is threaded through a boss 50 on inlet elbow C. The end of brake shaft 48 opposite from knob 49 engages the annular top end surface of inlet connector B to selectively maintain inlet elbow C in a desired rotated position relative to inlet connector B. Releasing brake shaft 48 by rotating knob 49 permits free rotation of elbow C about a vertical axis to direct a water stream from outlet 20 in a desired direction.

A first or proximate end portion 52 of U-shaped extension pipe D is rotatably received over horizontal end portion 42 of inlet elbow C with a sealing ring 53 interposed therebetween. The external peripheral surface of end portion 42 on inlet elbow C and the interior peripheral surface of first end portion 52 on extension pipe D have cooperating bearing races formed therein. Suitable radial holes in end portion 52 of extension pipe D permit installation of ball bearings between the races followed by closing of the holes with plugs 54, 55.

A releasable plunger assembly 56 is mounted in a suitable radial hole through first end portion 52 and boss 57 on extension pipe D. The inner end of plunger assembly 56 is received in a depression in the exterior surface of horizontal portion 42 on inlet elbow C. Two circumferentially-spaced depressions or blind holes are provided for receiving the inner end of plunger assembly 56 in the downwardly inclined lowermost position and the vertical elevated position of FIG. 2. Thus, the plunger assembly 56 releasably locks extension pipe D in either its full line lowermost position or its vertical shadow line position of FIG. 2.

A screw 58 threads into a suitable tapped radial hole in first end portion 52 on extension pipe D generally opposite boss 57. The inner end portion of screw 58 is received in a circumferential slot 59 in the exterior surface of horizontal portion 42 on inlet elbow C. Screw 58 engages the opposite ends of slot 59 to positively stop rotation of extension pipe D in its vertical or downwardly inclined positions. The ends of slot 59 are located to stop upward rotation of extension pipe D when it is in the vertical shadow line position of FIG. 2 and to stop downward rotation thereof when the extension pipe is in the solid line downwardly inclined position of FIG. 2. Extension pipe D rotates approximately 135° between its full vertical position and its downwardly inclined lowermost position.

Opposite second or distal end portion 62 on extension pipe D receives an eccentric sleeve 63 with a sealing ring 64 interposed therebetween. The external surface of second or distal end portion 62 and the interior surface of sleeve 63 have cooperating bearing races therein. A suitable radial hole in sleeve 63 permits installation of ball bearings between the races followed by closing of the hole with a plug 65.

Sleeve 63 has a cylindrical outer surface and a cylindrical bore therethrough but the axes of the two cylinders are not coincidental so that eccentricity is provided. This allows adjustment of the tension in a chain as will be described hereafter in connection with selective angular adjustment of the outlet elbow. A plurality of suitable circumferentially-spaced tapped radial holes in eccentric sleeve 63 receive set screws, only one of which is shown at 67, to lock sleeve 63 in its adjusted position against rotation on end portion 62 of extension pipe D.

Generally L-shaped outlet elbow E is rotatably received on eccentric sleeve 63 with a sealing ring 69 interposed therebetween. The exterior surface of sleeve 63 and the interior surface of outlet elbow E have suitable cooperating bearing races therein. Suitable radial holes in outlet elbow E permit installation of ball bearings between the races followed by closing of the holes with plugs 70 and 71. Outlet elbow E has a horizontal portion 74 that is rotatably mounted on second end portion 62 of extension pipe D, and a discharge portion 76 that extends radially of second horizontal axis 16 and has outlet 20 therein for discharging a water stream.

With the arrangement described thus far, extension pipe D can be rotated between its solid line lowermost position and its shadow line vertical position of FIG. 2 by releasing plunger assembly 56 and applying a lifting or lowering force to the extension pipe. The length of extension pipe D between first and second horizontal axes 14, 16 in FIG. 2 may be around 20 inches. It will be recognized that this dimension and the resulting change in elevation of the outlet may vary and should not be taken in a limiting sense.

Provision is made for selectively adjusting the angular position of outlet elbow E to vary the angle of the water stream being discharged relative to the horizontal. At the same time, provision is also made for maintaining the discharge angle of the water stream the same during raising and lowering movement of the extension pipe.

A gear member G includes a worm wheel 80 and a sprocket 82, and is rotatably received on first end portion 52 of extension pipe D. A worm gear housing 84 is attached to inlet elbow C beneath horizontal portion 42 thereof and has a worm gear assembly 86 that includes a worm gear drivingly engaged with worm wheel 80. Worm gear assembly 86 is attached to a shaft 90 that is rotatably mounted on housing 84 and has a handwheel 92 attached thereto. A handle 94 is attached to handwheel 92 by bolt 96.

Two circumferentially-spaced screws, only one of which is shown at 102 adjacent worm wheel 80, are attached to the outer periphery of the worm wheel to serve as stops when engaged by the worm gear. The two screws are spaced and positioned to provide rotation of outlet elbow E over an arc of about 135° between the extreme positions shown at 20*a* and 20*b* in FIG. 2.

Horizontal portion 74 of outlet elbow E has a sprocket 110 attached thereto, and a chain 120 extends around sprockets 82, 110. It will be recognized that a flexible driving element such as a belt can be used with pulleys instead of a chain and sprockets. Rotation of handwheel 92 and the worm gear imparts rotation to worm wheel 80 and sprocket 82. Rotation of sprocket 82 drives chain 120 to rotate sprocket 110 and outlet elbow E. This permits adjustment of the angle that the water stream makes with the horizontal as it is discharged through outlet 20. Rotation of handwheel 92 selectively moves outlet elbow E between its extreme positions illustrated at 20*a*, 20*b* in FIG. 2. Eccentric sleeve 63 permits variation in the distance between first and second horizontal axes 14, 16 to adjust the tension in chain 120.

A plunger assembly 126 is received in a suitable hole through a boss 128 on inlet elbow C and engages a suitable ramped arcuate recess in an end face of worm wheel 80. The ramped arcuate recess has an end abutment that engages the plunger assembly 126 to prevent lowering of discharge elbow to a position in which outlet 20 is less than 35° above the horizontal. This is a safety feature to prevent the water stream from being directed too close to the horizontal because the reaction force of the water would topple the monitor when it is on the ground base F. When the monitor is attached to a flange mount on the deck of a fire fighting apparatus, the plunger assembly 126 can be pulled to release it from engagement with the stop in the end face of worm wheel 80 so that the water stream can be lowered below a position 35° above the horizontal. When mounted on the deck of an apparatus, outlet elbow may be moved to the full range of positions illustrated at 20*a*, 20*b* in FIG. 2.

When extension pipe D is rotated between its downwardly inclined lowermost and vertical positions, sprocket 82 and worm wheel 80 remain stationary. This is because worm wheel 80 and sprocket 82 cannot rotate without rotation of the worm gear. Thus, chain 120 cannot move linearly during rotation of extension pipe D because sprocket 82 does not rotate. However, rotation of extension pipe D causes relative movement between the chain and sprocket 110 on outlet elbow E. This relative movement causes rotation of outlet elbow E along the chain a degree that is equal and opposite to the degree and direction of rotation of extension pipe E. For example, if outlet elbow E is positioned with outlet 20 extending horizontally in the solid line position in FIG. 2 when extension pipe D is in its lowermost position, outlet 20 will remain in that horizontal position during movement of extension pipe D to its vertical position. Counterclockwise rotation of extension pipe D about first horizontal axis 14 in FIG. 1 results in clockwise rotation of outlet elbow E. The angle through which outlet elbow E rotates is the same as the angle through which extension pipe E rotates. The chain and sprockets provide a motion translation mechanism that translates rotation of the extension pipe into rotation of the outlet elbow in an opposite direction, and with the angles of rotation being the same.

An inner guard member 132 cooperates with outer cover shield 12 to shield the chain and sprockets. A handle 140 attached to inlet elbow C by a bolt 142 facilitates lifting of the entire monitor A from base F. Pins 25, 26 may be removed to release inlet connector B from ground base F and this frees the entire monitor assembly A for movement to another location, such as a flange mount on the deck of a fire fighting apparatus, or for replacement or repair. Extension pipe D has a suitable tapped drain hole generally indicated at 150 that receives a drain plug assembly 152. A suitable enlarged opening in a boss 154 on cover 12 provides access to the drain plug.

Although the invention has been shown and described with reference to a preferred embodiment, it is obvious that equivalent alterations and modifications will occur to others skilled in the art upon the reading and understanding of this specification. The present invention includes all such equivalent alterations and modifications, and is limited only by the scope of the claims.

I claim:

1. A fire fighting monitor comprising inlet and outlet members connected to opposite ends of an extension pipe, said inlet member being rotatable about a vertical axis, said extension pipe being rotatable about a first horizontal axis relative to said inlet member, said first horizontal axis being in a fixed vertical position, said outlet member having an outlet and being rotatable about a second horizontal axis relative to said extension pipe, and a mechanical motion translation mechanism that extends around and between said first and second horizontal axes and automatically maintains the direction of said outlet constant during and in response to rotation of said extension pipe about said first horizontal axis by rotating said outlet member a degree that is equal and opposite to the degree of rotation of said extension pipe.

2. The monitor of claim 1 wherein said extension pipe is U-shaped.

3. The monitor of claim 2 wherein said inlet and outlet members are L-shaped.

4. The monitor of claim 1 wherein said extension pipe is rotatable about said first horizontal axis between a lowered position extending downwardly of the horizontal from said first horizontal axis and an elevated position extending vertically upwardly from said first horizontal axis.

5. The monitor of claim 1 wherein said outlet member is rotatable between downward and upward discharge positions in which said outlet is directed downwardly of the horizontal and vertically upward.

6. The monitor of claim 1 wherein said mechanical motion translation mechanism is selectively adjustable to vary the discharge direction of said outlet by rotating said outlet member relative to said extension pipe about said second horizontal axis without rotation of said extension pipe about said first horizontal axis.

7. The monitor of claim 1 wherein said outlet member has a vertical position in which said outlet member extends vertically upward from said second horizontal axis, said outlet member being rotatable in one direction from said vertical position through an angle of at least 135°.

8. The monitor of claim 1 wherein said extension pipe has a vertical position in which it extends vertically upward from said first horizontal axis, said extension pipe being rotatable in one direction from said vertical position through an angle of at least 135°.

9. A fire fighting monitor including an inlet elbow rotatable about a vertical axis and having an extension pipe attached thereto for rotation about a vertically fixed first horizontal axis, said extension pipe having a distal end portion spaced from said inlet elbow, an outlet elbow attached to said distal end portion for rotation about a second horizontal axis, said extension pipe being rotatable about said vertically fixed first horizontal axis between a lowered position and a raised position extending upwardly from said first horizontal axis to raise the elevation of said outlet elbow.

10. The monitor of claim 9 wherein said extension pipe is U-shaped.

11. The monitor of claim 9 wherein said extension pipe is rotatable about said first horizontal axis between a vertical position and a lower position below the horizontal.

12. A fire fighting monitor including an inlet elbow, an extension pipe having a proximate end portion attached to said inlet elbow for rotation about a first horizontal axis, a first sprocket rotatable on said proximate end portion of said extension pipe, said extension pipe having a distal end portion spaced from said inlet elbow, an outlet elbow attached to said distal end portion for rotation about a second horizontal axis, a second sprocket non-rotatably attached to said outlet elbow, a chain extending around said first and second sprockets, and said extension pipe being rotatable between a lowered position and a raised position extending upwardly from said first horizontal axis to raise the elevation of said outlet elbow.

13. The monitor of claim 12 including a worm gear drive for selectively rotating said first sprocket to move said chain and rotate said second sprocket and said outlet elbow to vary the angle that a water stream discharged from said outlet elbow makes with the horizontal.

14. The monitor of claim 12 including an eccentric sleeve interposed between said distal end of said extension pipe and said outlet elbow for adjusting the tension in said chain.

* * * * *